United States Patent [19]
Heinrichs et al.

[11] Patent Number: 6,092,722
[45] Date of Patent: Jul. 25, 2000

[54] METHOD AND DEVICE FOR THE AUTOMATIC IDENTIFICATION OF COMPONENTS OF MEDICAL APPARATUS SYSTEMS

[75] Inventors: Jean-Pierre Heinrichs, Bretten-Diedelsheim; Ehrenfried Bitrolf, Knittlingen-Kleinvillars; Martin Dolt, Knittlingen, all of Germany

[73] Assignee: Richard Wolf GmbH, Knittlingen, Germany

[21] Appl. No.: 08/898,692

[22] Filed: Jul. 22, 1997

[30] Foreign Application Priority Data

Jul. 23, 1996 [DE] Germany ............ 196 29 646

[51] Int. Cl.[7] .................................................. G06K 5/00
[52] U.S. Cl. ........................................ 235/375; 235/380
[58] Field of Search ................... 235/382, 492, 235/441, 449, 499, 486, 375, 380, 487

[56] References Cited

U.S. PATENT DOCUMENTS

| | | | |
|---|---|---|---|
| 4,795,898 | 1/1989 | Bernstein et al. | 235/488 |
| 4,960,983 | 10/1990 | Inoue | 235/449 |
| 5,436,441 | 7/1995 | Inoue | 235/487 |
| 5,444,222 | 8/1995 | Inoue | 235/380 |
| 5,698,838 | 12/1997 | Yamaguchi | 235/492 |

FOREIGN PATENT DOCUMENTS

| | | |
|---|---|---|
| 0 534 198 A2 | 3/1993 | European Pat. Off. . |
| 37 42 900 C2 | 10/1990 | Germany . |
| 40 20 522 A1 | 1/1992 | Germany . |
| 41 13 556 C2 | 2/1996 | Germany . |

*Primary Examiner*—Thien Minh Le
*Attorney, Agent, or Firm*—Cohen, Pontani, Lieberman & Pavane

[57] ABSTRACT

The invention relates to a method and apparatus for the automatic identification of components of medical apparatus systems, in particular, components of endoscopy systems. There is provided a unit which is separate from at least one of the components (30a, 30b) to be identified, this unit includes a write-read head. This unit may for example be one of the system components such as a camera head (18) in a video endoscope system. Each component to be identified includes a writable and readable data carrier which stores data signals indicating component parameters. Contents of the data carrier can be read in by transmission of the data to the write-read head from the separate unit and may here be registered and where appropriate, activate control and/or regulation procedures. According to the invention, the employed data transmission system is a touch-free system, with which the energy for reading out or registering the data into the data carrier of the components is transmitted by induction from the write-read head of the separate unit to the component. The separate component further contains a modulation-demodulation device with which the signals to be transmitted to the component are modulated and the data signals received by the component are demodulated. A video camera (15a) connected to the camera head (18) may, on account of the data read out by the components (30a, 30b), be automatically adapted to their specifications.

26 Claims, 6 Drawing Sheets

METHOD AND DEVICE FOR THE AUTOMATIC IDENTIFICATION OF COMPONENTS OF MEDICAL APPARATUS SYSTEMS

BACKGROUND OF THE INVENTION

The invention relates to a method and device for the automatic identification of components of medical apparatus systems. More specifically, the invention relates to a data carrier on a medical device and a method of automatically identifying, reading, and writing to the data carrier.

In the art, various methods for identifying components are known, these various methods work with different transmission and coding methods. As examples, there are only here cited those methods, for the identification of components, in stock keeping which primarily works with optically or magnetically readable bar codes, and similar methods for the arranging of goods, which are used, for example in mail-order companies and large department stores. Other examples are those methods and devices for the identification of moving objects, such as for the identification of vehicles such as airplanes and boats and land vehicles, which by way of electromagnetically transmitted interrogation signals, interrogate an identification code stored in a transponder in the component, i.e in the vehicle, this code then being actively or passively sent to the interrogating station. These common identification systems operate without contact but require, besides the systems interrogating the bar code, an energy source in the interrogated object.

A touch-free energy and data transmission method concerning an inductive coupling is also known in which a write-read head and the component to be interrogated each include a high frequency coil so that the component to be interrogated and the separate unit comprising the write-read head, with the identification procedure, act like a loosely coupled transformer. With the interrogating, the high frequency coil of the write-read head produces a high frequency field. The coil in the component receives the field. The coil in the component also supplies power to an electronic memory, which is connected to the coil and serves as a data carrier. Data in this memory is read out through a memory read-out and control logic. The read out data is transmitted to the high frequency coil of the components. This coil together with a capacitor form an oscillating circuit, the oscillation of which is modulated by the data read out from the memory. This modulation is in turn transmitted to the high frequency coil of the write-read head, where it is recognised and further transmitted to a receiving circuit. This type of modulation is known as absorption modulation and is for example employed in radar technology. Finally, such an absorption modulation represents a pulse width modulation.

Building on this principle, an identification method may also be realized in which the memory which is contained in the component as a data carrier not only can be read out, but can also be written to. Apart from the pure transmission of identification data it is also possible to transmit instruction signals to the data carrier, and to the component, to control functions of the data carrier and the component.

The identification system known from the previously cited EP-A-0 534 198 is employed with an endoscope. On the endoscope side, a memory for special ratings of the endoscope and a control apparatus, which can be coupled to the endoscope via contacts, are provided. The ratings can be interrogated to obtain compensation parameters for the operating parameters, to be set on the control apparatus. Such ratings which are stored in the data carrier of the endoscope, apart from compensation parameters, may also denote other parameters such as operation duration, maintenance period, serial numbers or likewise.

Further, from DE-C-37 42 900, an endoscope arrangement with a video endoscope and a control apparatus for the image sensor is described. Ratings of the endoscope, in particular the number of image spots of the image sensor, are deposited in a memory on the endoscope side which is arranged within the connector, with which the video endoscope is connected to the control apparatus. By interrogating the stored ratings, the control apparatus may then be individually adapted to the endoscope. The interrogation is effected via the contacts of the connector.

In medicine technology, in particular in endoscopics, to this day there has been no possibility of automatically interrogating and registering, without touch, ratings of several, in particular, of exchangeable components belonging to a medical apparatus system, by way of a secure method particularly suited to medicine technology. There has also been no possibility of effecting a change of the ratings of the components.

Particularly in medical endoscopics it is often necessary to prepare or sterilize optics and objectives with clinical use. Also, in the framework of quality assurance and ISO certification of clinics, preparation and sterilization cycles must be instrument-specifically documented. Only this documentation permits a clear assessing of the performance capability and reliability of the above mentioned components.

BRIEF SUMMARY OF THE INVENTION

It is therefore the object of the invention to put forward a method and device for the automatic identification of components of medical apparatus systems, in particular components of endoscopy systems, with which by way of an energy-free, touch-free transmission, an interrogation of identification data and also a reregistering thereof is made possible.

Also the method and apparatus are to permit, by recording the characteristic ratings of the respective components, an automatic adaptation of a subsequent apparatus which can be connected to the respective components, as e.g. with video cameras, an adaptation of the image size, a distortion correction, an adaptation to the light regulating characteristics, an adaptation to the aperture of the employed light source, etc.

According to a first aspect, a method for the automatic identification of components of medical apparatus systems, in particular, components of endoscopy systems, in which there are provided, in the component, for storing parameters at least of this component, a data carrier which can be written and read by a separate unit; and in the separate unit, at least a write and read control device for the repeatable writing and reading of the data carrier, characterized by the following steps:

a) preparing a touch-free energy and data transmission system in the component and in the separate unit, for transmission of data indicating parameters, between the data carrier of the component and the separate unit in both directions;

b) positioning the component in the proximity of the separate unit;

c) activating an identification procedure, in which, touch-free, an identification interrogation signal is transmitted from the separate unit to the component via the data transmission system;

d) receiving the identification interrogation signal by the component and reading out at least an identification parameter from the data carrier;

e) transmitting to the separate unit an answer signal indicating the identification parameter; and f) receiving and registering the identification parameter by the answer signal in the separate unit.

Advantageously, to the method according to the invention, there may be added a further step which activates a write procedure for changing or newly storing data of one or several parameters into the data carrier of the component, transmits a corresponding write signal via the data transmission system from the separate unit to the component; in the data memory there, changes or registers one or more parameters corresponding to the write signal and thereupon sends a receipt signal from the component via the data transsmission system to the separate unit, and ends the activation of the write procedure on the receipt signal. Further, an activation of the indentification and or write procedure is possible by an operation step on the separate unit.

The method may be developed by a monitoring step for monitoring the identification and/or write procedure by an operating person. Purposefully, the operating person carries out the monitoring on the monitor.

The separate unit containing the write and read control device may merely be installed for activating or carrying out the identification and/or write operations and where appropriate carrying out the monitoring of the operation also for different components. For this, the separate unit may also be connected to an overriding computer.

Alternatively it is foreseen that the separate unit is a part of the respective medical apparatus system. With an endoscope system targeted as a particular application case, the separate unit may for example be a camera head of a video camera.

A further advantageous step of the method according to the invention lies in carrying out control and/or regulating procedures in the separate unit on account of the parameter data transmitted from the component to the separate unit.

According to a further aspect of the invention there is provided a device for the automatic identification of components of medical apparatus systems, in particular components of endoscopy systems, with a unit which is provided separately from the components and which comprises a read-write control device, and a writable and readable data carrier in each component for storing parameters of the respective components in the form of data signals, wherein contents of the data carrier can be read out and registered by the read-write control device and can at least be stored in the separate unit, characterized by a touch-free energy and data transmission system, provided in the component and the separate unit, for transmission of data signals between the separate unit and the data carrier of the component in both directions, a write-read head which is connected to the read-write control device, a signal producing and modulation-demodulation unit in the separate unit which is connected to the read-write control device and the write-read head in order to modulate or demodulate data signals, connected to the data carrier in the component, an emitting-receiving device for emitting and receiving data signals from or in the component, wherein all the devices in the component are fed by the separate unit by means of the transmission procedure and have no energy source of their own.

Preferably the data transmission system is based on an inductive high frequency transmission. Furthermore, the transmitted data signals are subjected to pulsed period modulation by means of the data transmission system. The so modulated data signals are transmitted between the component and the separate unit and vice-versa in a frame structure which contains at the beginning, an identification code, following thereafter, one or more data posts and at the end, a checking code at least for recognizing errors.

The separate unit has an operating device for activating an identification and/or writing operation. The operating device may be connected to the separate unit or may alternatively be an integral part of it.

Further, the monitor may be connected to the separate unit. The operating device and the monitor may also be parts of an over-riding computer system connected to the separate unit.

BRIEF DESCRIPTION OF THE DRAWINGS

In the drawings, wherein like reference numerals denote similar elements throughout the several views.

DETAILED DESCRIPTION OF THE PREFERRED EMBODIMENTS

Figure 1:
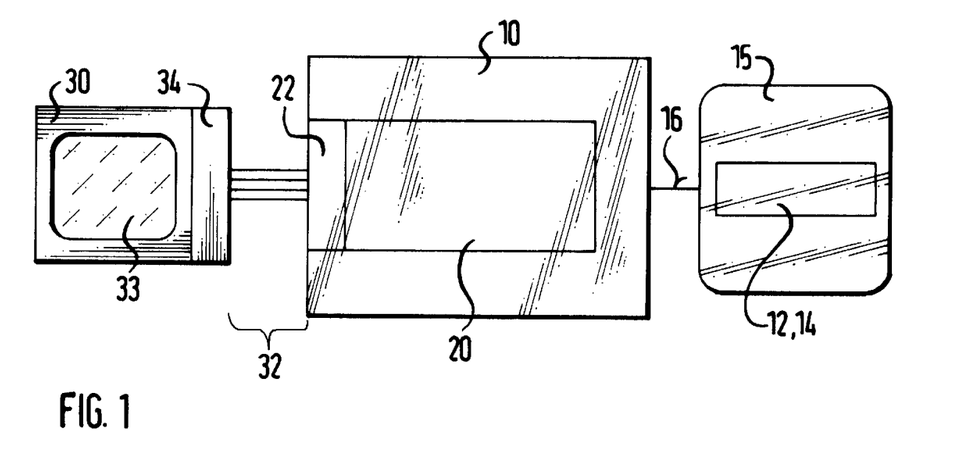
FIG. 1 is a block diagram of an embodiment of the automatic identification of components of the present invention.

Referring to FIG. 1, the present invention includes at least one unit 10 provided separately from at least one system component 30, said unit comprising a read-write control device 20. The read-write control device 20 is connected to a write-read head 22 which is described further below. The schematically indicated component 30 comprises a data carrier 33, which can be registered and read out, for storing up data signals which indicate parameters of at least these components.

A touch-free energy and data transmission system 32, as will be described later, comprises the write-read head 22 of the separate unit 10, a transmission stretch not shown separately and in the component 30, an emitter-receiver device for emitting and receiving data signals from or in the component. Further, the emitter-receiver device 34 is connected to the data carrier 33 in the component 30. The contents of the data carrier 33 can be read out and registered by the read-write control device 20 and are at least storable in the separate unit 10. Further below it is however cited that contents, which are read from the data carrier 33 of the component 30, may also serve the activation of regulating and control procedures in the separate unit 10 and/or a controlled unit 15 connected to this unit.

The data transmission system 32 is so set up that all devices in the component 30 are fed by the separate unit 10 by means of the data tranmission procedure and that they have no energy source of their own.

Figure 2:
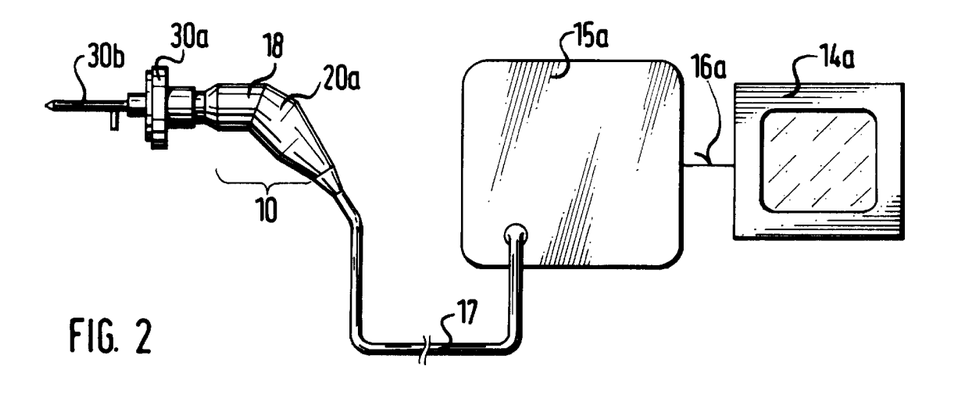
FIG. 2 is a schematic diagram of another embodiment of the automatic identification of components wherein the component is an endoscope.

FIG. 2 shows an application example of the method according to the invention or the device according to the invention for the automatic identification of components of a medical apparatus system, wherein in this example an endoscopic system is represented.

The controlled device here is a video camera 15a which is connected to a monitor 14a via a cable 16a. The video camera 15a is further connected to a camera head 18 by a cable 17. In one part of the camera head 18 there is accommodated a separate unit 10' which thus in this example is a system component and which contains a read-write unit 20a and a write-read head 20a which is not shown in FIG. 2 and described by way of FIG. 1.

In FIG. 2 there are represented two components which can be identified with the device according to the invention, that is to say an objective 30a and an endoscope optic 30b. Both components 30a, 30b each contain a data carrier 33 which however in FIG. 2 is not separately represented. In the data carrier of the objective 30a and also in the data carrier of the endoscope optic 30b, not only can the serial numbers of the respective components and the time period of the preparation cycle be stored, but also data signals which permit an automatic adaptation of the camera head 18 and of the video camera 15a connected thereto, as for example the adaptation of the image size and the correction of the distortion, the adaptation of the light regulating characteristics, the limiting of the power and the aperture adjustment to a light source.

Figures 3, 4:
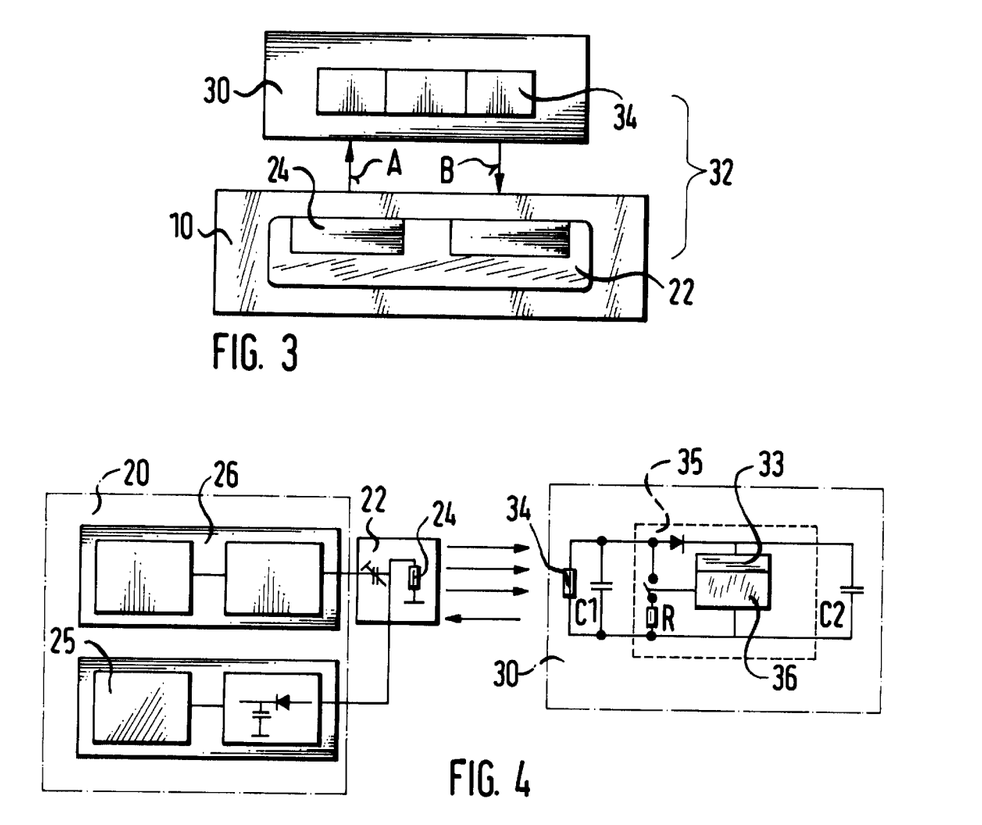
FIG. 3 is a schematic diagram of a component and a separate unit of the embodiment of FIG. 1.
FIG. 4 is a schematic diagram showing a specific example of the component and separate unit of FIG. 3.

FIG. 3 shows an induction coil arrangement of the touch-free transmission system used with the invention. In the separate unit 10 there is located a write-read head 22 formed as a read-write coil. This may be designed with or without an iron or ferrite core. The write-read head 22 contains an emitter coil 24 in order to transmit energy to the component 30 when effecting a data transmission (arrow A). The same coil 24 is used in order to receive the data signals sent back from the component (arrow B). In the component 30, the emitter-receiver device 34 likewise comprises a coil with or without a ferrite core. For a secure energy and data transmission, a good coupling between the write-read head 22 in the separate unit and the coil 34 is important, since the magnetic field lines only have a small reach. At the same time the coil 24 of the separate unit 10 and that of the data carrier in the component 30 perform as a loosely coupled transformer when the emitter-receiver device 34 is within an operational proximity of the coil 24. Generally a distance of about 100 mm between the coil of the write-read head and that of the data carrier is seen as sufficient.

The coil of the reading head produces a magnetic high frequency field. The coil of the data carrier receives the field, supplies the data carrier with energy and takes care of the subsequent transmission of data stored in the data carrier. The write-read memory serving as a data carrier and an associated control logic may be integrated together as a switch on a chip (cf. FIG. 4).

FIG. 4 shows a block diagram of a principle circuit of a reprogrammable touch-free high frequency transmission method, as is preferably used with the present invention for the identification of components of medical systems. The circuit, represented in FIG. 4 as a block diagram, of the coil 34 and of the chip 35 in the component 30, is known per se and is thus not described in more detail. Essential is that the coil 34 together with capacitors C1, C2 form an oscillating circuit which, on data transmission, is supplied with energy from the coil 24 of the write-read head 22. Then the control logic 36, which is integrated together with the data carrier 33 in the chip, switches a resistance R on and off.

The energy consumption of the chip changes with the data, and this passive modulation is transmitted via the oscillating circuit, consisting of the coil 34 and the capacitors C1, C2, back to the coil 24 in the separate unit 20. The modulated signals may be demodulated in the write-read head 22. For this the read-write control device 20 of the separate unit 10 comprises a signal producing and modulation unit 26 and a demodulation unit 25. The circuit arrangement of the units 25, 26 in the read-write control device 20 is known per se and is not described in detail here. The modulation type employed is also known as "absorption modulation".

Figure 5:
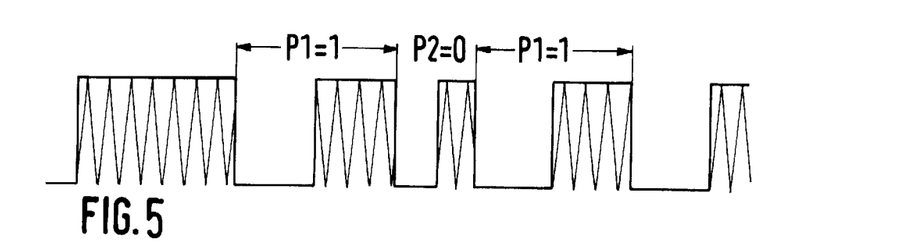
FIG. 5 is a graph showing an example of pulsed period modulation used in the system of FIG. 4.

FIG. 5 shows, with the help of this modulation type, modulated data signals P1 corresponding to a logic "1" and a data signal P2 corresponding to a logic "0", which in each case comprise different impulse period times. The carrier frequency, which is for example 125 kHz serves the previously mentioned energy supply of the data carrier. The oscillating circuits employed are tuned to the carrier frequency. This switching not only allows the return transmission of the data signals stored in the data carrier 33, such as characteristic quantities etc., but also the reregistering of data into the data carrier. For this, apart from data, commands are also transmitted from the signal producing and modulation-demodulation units 25, 26 represented in FIG. 4 to the data carrier 33 of the component 30, in order to control the function of the data carrier.

Figure 6:
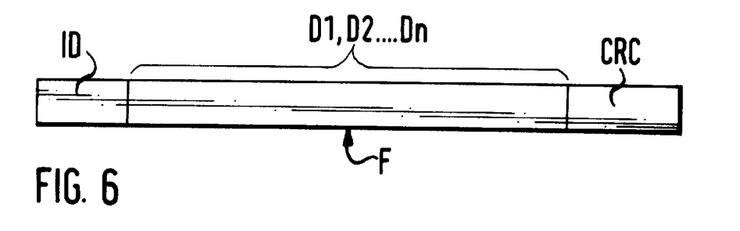
FIG. 6 is a frame structure for data signals transmitted the component and separate unit of FIG. 4.

FIG. 6 shows a frame structure F, suitable for the data transmission in the transmission system described up to now, which comprises an identification code ID at the beginning of the frame, one or more data posts D1, D2 . . . $D_n$ which follow the identification code ID, and a checking code CRC at the frame. The checking code CRC serves to recognize errors in the data posts.

Figure 7:
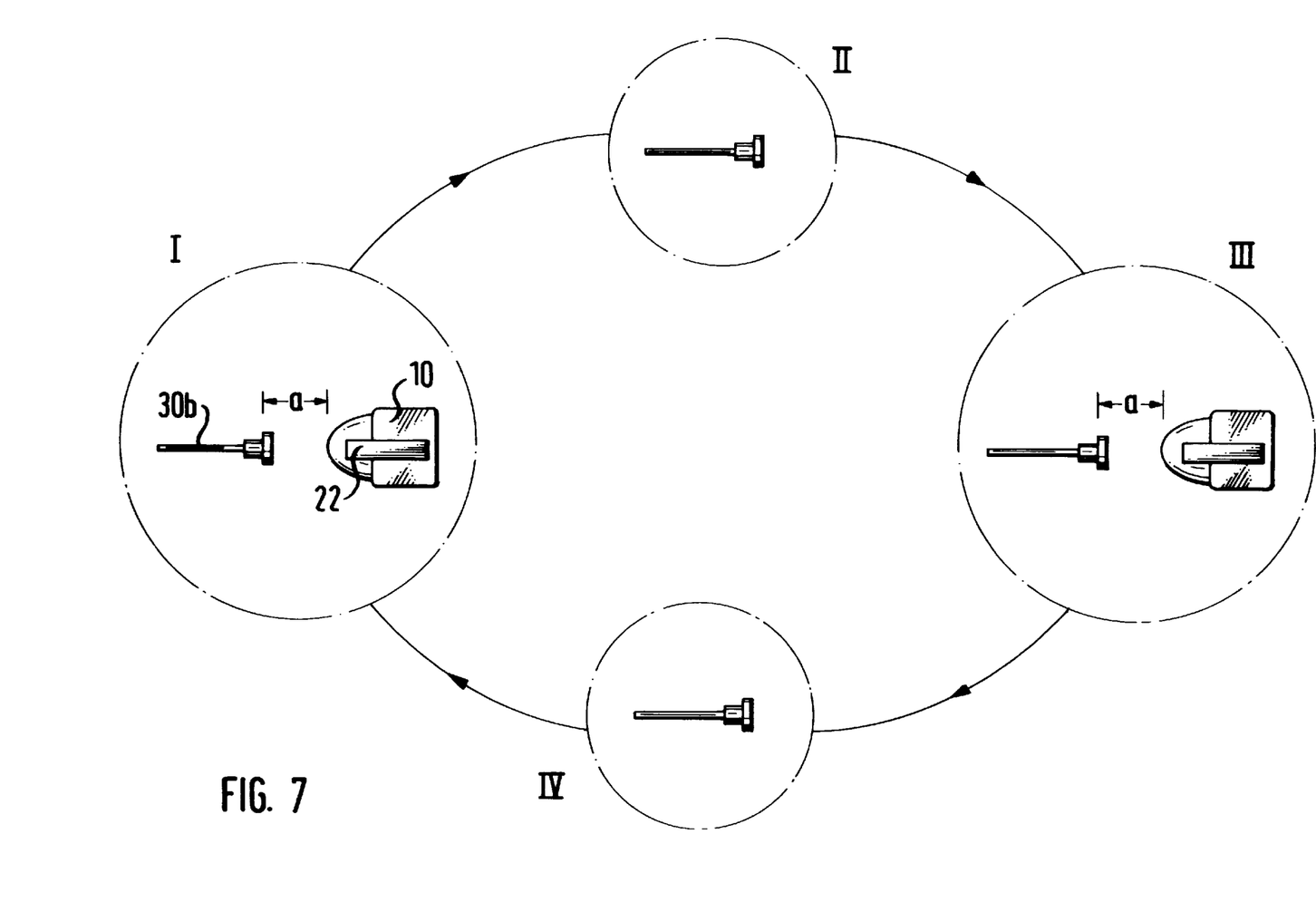
FIG. 7 is a cyclical flow diagram showing a preparation cycle of an endoscope having a automatic identification data carrier of the present invention.

In FIG. 7 there is shown an example of the use of a device according to the invention for the automatic identification of an endoscope equipped with a previously described data carrier in a repreparation cycle.

In the stage I an employed endoscope 30b is brought into the region of a write-read head 22 of a separate unit 10 (distance a is about 100 mm). The separate unit 10 may be part of a sterilization apparatus. The data transmission delivers e.g. the serial numbers of the component, i.e. of the endoscope 30b, which are read and stored in the sterilization apparatus. Further, the data signals read out from the data carrier of the endoscope 30b may also contain instructions for the sterilization cycle whose parameters these instructions control or regulate.

In stage II the sterilization apparatus is loaded with the endoscope to be sterilized and the sterilization procedure is carried out. In stage III the endoscope is once again guided to the write-read head located in the sterilization apparatus. Now for example, the number of sterilization cycles stored in the endoscope is increased by one. With the data transmission carried out at the same time there is thus a reading and writing of the data carrier in the endoscope. Finally the endoscope in stage IV is used again.

In the case of repair, the data carrier of the endoscope may be read out at the repair location. The stored data may serve the checking of the guarantee details. After a repair, the number of repair cases stored in the endoscope may be increased by 1. For this, in the repair department there is available a separate unit 10 according to the invention, which in the same manner as previously described, activates and carries out a data transmission between the separate unit and the data carrier of the endoscope.

It is to be noted that with the application example mentioned above and in FIG. 7, no operator-controlled activation and data transmission is shown. This however makes sense in any case, when selective data values are to be registered in the data carrier of the component and the number values stored in the data carrier are incremented or decremented.

Figure 8:
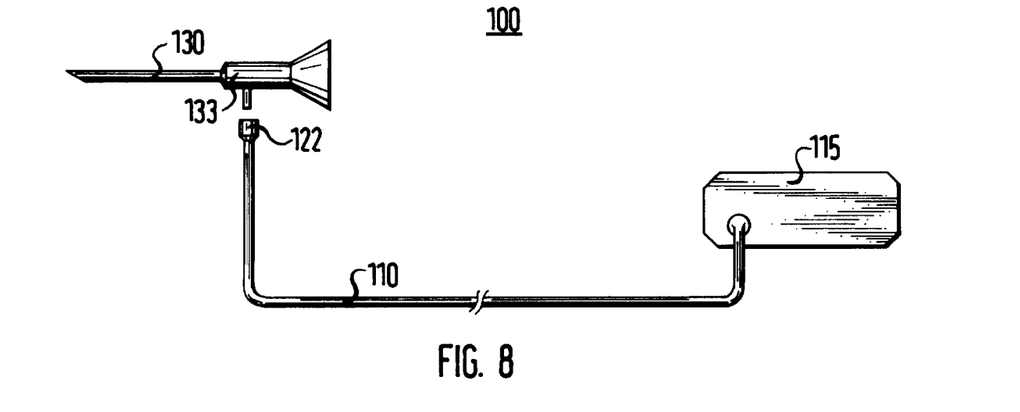
FIGS. 8–12 are schematic diagrams each showing a different embodiment of an endoscope having an automatic identification data carrier of the present invention.

In FIG. 8 there is shown an endoscopy system in a first configuration 100, which concerns a further application example of the device and the method according to the invention. An endoscope 130 with a data carrier 133 according to the invention is connected to a light source 115 via a fiber optic cable 110 equipped with a read-coil 122 according to the invention, said light source being seen as a controlled or regulated apparatus in the sense of the above description. The light source may be automatically be adapted by way of the data read out from the components 130 and 110 with the data transmission system according to the invention or read out by the data carriers 133, 122 located in the components, this data concerning the emitted maximum light energy, the aperture and other parameters concerning the fiber optic cable and the endoscope employed. In particular, with light sources with lamps, which comprise a heavily medium accentuated radiation profile, such as e.g. Xenon short arc lamps, for improving the radiation characteristics, there may be provided that graduated filters, matted lenses or partly pervious components are pivoted into the beam path automatically on account of this data.

Figure 9:
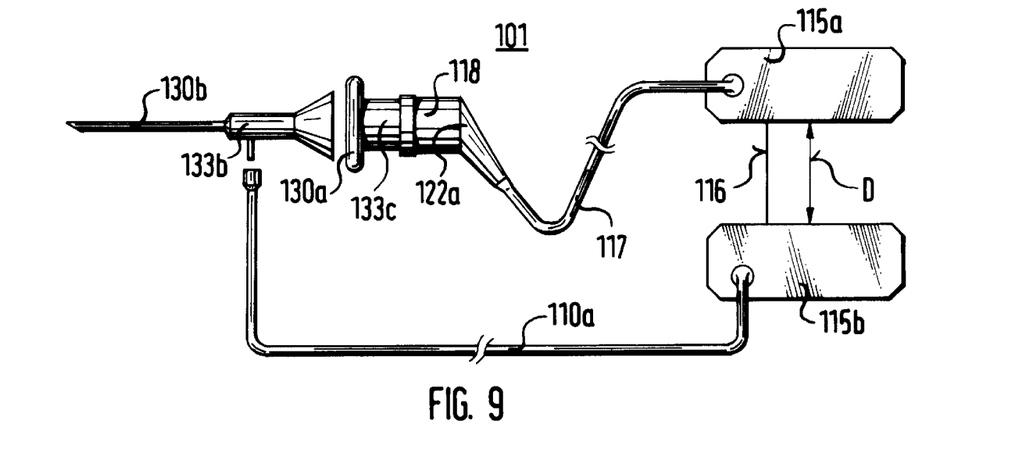

A further application example is represented by the configuration 101 shown in FIG. 9, which may be seen as an alternative to the system 100 shown in FIG. 8. The upper part of the endoscopy system 101 is similar to that shown in FIG. 2, wherein the monitor is left out. An endoscope 130*b* with a first data carrier 133*b* is coupled with its proximal end to the distal end of an objective 130*a* which comprises a second data carrier 133*c*. The objective 130*a* is on the one hand connectable with its proximal end to a camera head 118 which comprises a read-coil 122*a* according to the invention. The camera head 118 is, via a conductor system 117, coupled to a video camera 115*a* which is equipped with a function for the automatic adaptation to the camera head, the objective and the endoscope applied in each case, in order in this way to permit an adaptation to the image size, the correction of the distortion, the adaptation of the light regulating characteristics, the limitation of the power and an adaptation of a light source 115*b*. This light source 115*b* is coupled in the usual manner to the associated connection of the endoscope via a fiber optic cable 110*a*. The light source 115*b* receives the data necessary for the adaptation via the data transmission stretch 116 (arrow D), which is preferably formed as a bidirectional data route. Due to the data which may be transmitted via the data transmission stretch 116 from the video camera 115*a* to the light source 115*b*, the distal connection of the fiber optic cable 110*a* does not need a write-read head, since the data to be transfered reaches the light source 115*b* via the data route 116.

Figure 10:
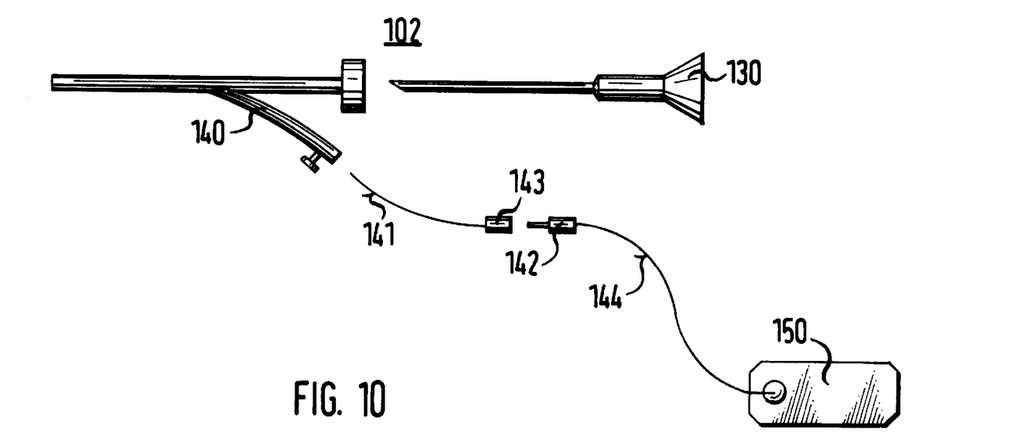

In FIG. 10 there is shown an application example with an electrosurgical high-frequency system 102. Into a trocar sleeve or an operating lumen 140, a HF probe or a thermo-coagulation probe 141 may be proximally introduced, said probe being provided with a data carrier 143 at its proximal end. The high frequency power is led from a high frequency power generator or a thermo-coagulation control device 150 through a cable 144, which is equipped at its distal end with a write-read head 142 according to the invention. In this way power and/or frequency, pulse width etc., at the high frequency power generator 150, may be adapted to the HF-probe 141 according to the data stored in the data carrier 143. An endoscope 130 also described in FIG. 10 may also be introduced into the trocar sleeve or the operating lumen 140 in addition or instead of the HF-probe 141, and thus be coupled. The endoscope 130 may also have a data carrier roughly according to FIG. 2, 8 and 9.

Figure 11:
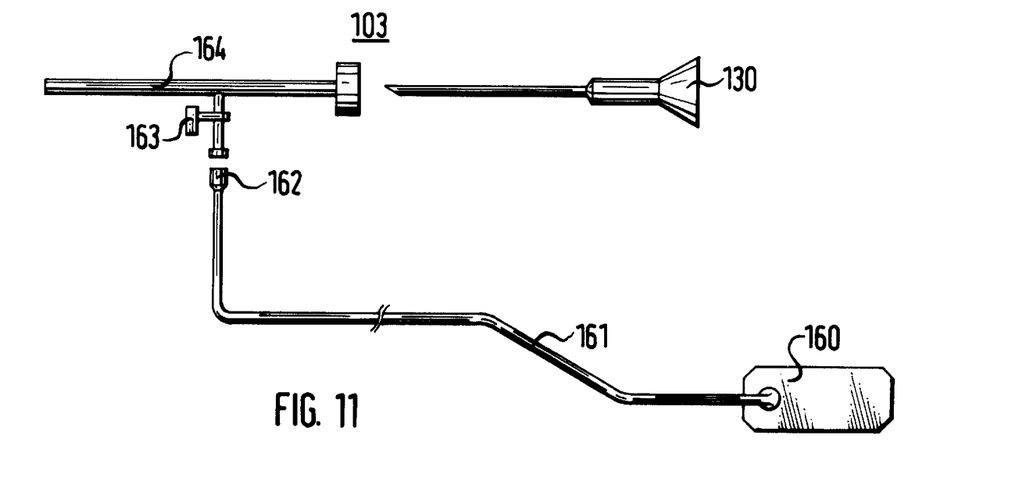

With the application example 103 shown in FIG. 11, an insufflation control apparatus 160 is connectable to an associated connection of a trocar sleeve 164 via a pneumatic hose 161. The trocar sleeve 164 is equipped at this connection with a data carrier 163, whilst the distal end of the pneumatic hose 161 is provided with a write-read head 162 according to the invention. In this manner, by way of the data stored in the data carrier 163 of the air connection of the trocar sleeve 164, the insufflation control apparatus 160, with regard to the pressure produced, the pressure impulses etc., may be automatically adapted to the trocar sleeve employed.

Figure 12:
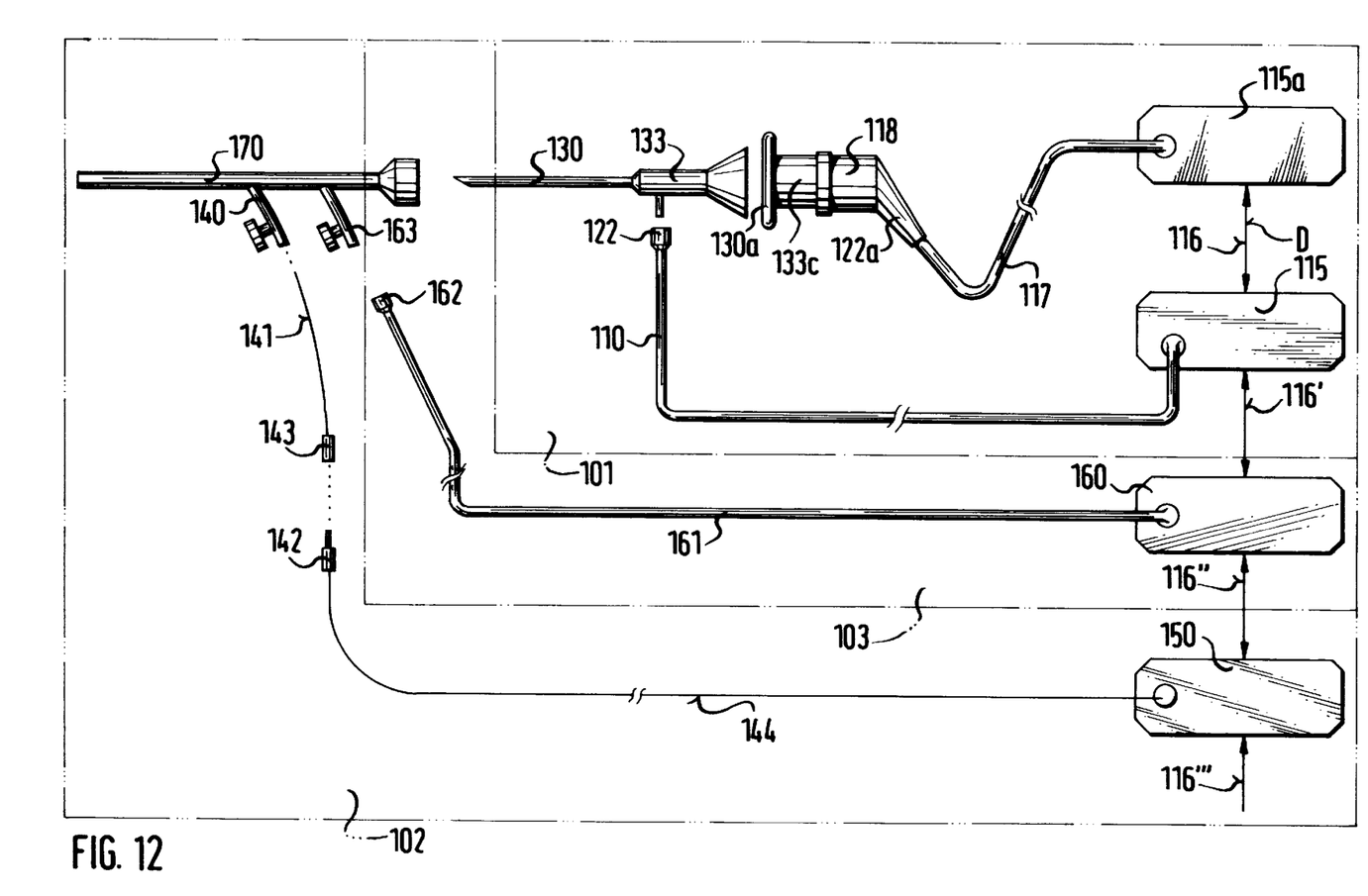

Finally in FIG. 12 there is shown a combined endoscopy system from those application examples 100 to 103 shown in FIG. 8 to FIG. 11. The video camera 115*a* with automatic adaptation is connected to a light source 115 likewise with automatic adaptation which in turn is connected to an insufflation aparatus 160 which in turn is connected to an electrosurgical high frequency generator 150 with automatic adaptation, these connections being made by the respective data transmission stretches 116, 116' and 116". The trocar sleeve is, at least at its air connection to which the insufflation hose is connected, equipped with a data carrier according to the invention. The distal end of the insufflation hose comprises a read-write head according to the invention. The further components shown in FIG. 12 are identical or equivalent to those correspondingly described in FIGS. 8 to 11 and have the same reference numerals.

Alternatively individual or several components/functional units of the system shown in FIG. 12 may remain without data carriers or write-read coils. With these alternatives the relevant information is transmitted via the data transmission stretches 116, 116', 116" and 116'". Of course further data transmission stretches may in each case be provided between the controlled apparatus 115, 115*a*, 150 and 160 and further apparatus.

Also system components, which in general are not in electrical contact with the control apparatus or likewise, such as purely mechanical components, e.g. endoscopes, objectives or also probes, may be provided with writable and readable memories for the identification according to the invention of the components.

Energy as well as data transmission is effected without touch and contact-free. This is then particularly advantageous since with many endoscope systems a direct voltage supply is not wanted or is dangerous.

The previous application examples of the invention described by way of FIGS. 8 to 12 make clear that the method according to the invention and the device for the identification of components of medical apparatus systems may also be applied in combination with customary data transmission methods, just as they can be used with the data routes 116 according to FIG. 9 and 116' 116" 116'" according to FIG. 12. The transmission method without touch employed in the invention may also be combined with a contacting transmission method similar to the previously mentioned EP-A-0 534 198.

Moreover the invention is not limited to the automatic identification of components in endoscope systems. Advantageously the invention may also be applied to other medical apparatus systems which require a sterilization and/or preparation of their system components and with which a multitude of different specific components may be employed.

What is claimed is:

1. A method for automatically identifying a component of a medical endoscopy system using data stored on a data carrier of the component and identifying the component, comprising the steps of:

effecting an inductive coupling between the data carrier of the component and a separate control unit by positioning the data carrier within an operational proximity of the separate control unit for bidirectional communication between the data carrier and the separate control unit via the inductive coupling;

activating an identification procedure by transmitting an identification interrogation signal from the separate control unit to the component via said inductive coupling;

receiving the identification interrogation signal at said component;

reading an identification parameter from the data carrier in response to said receipt of the identification interrogation signal;

transmitting, from the data carrier to the separate control unit via the inductive coupling, an answer signal indicating the identification parameter read from the data carrier; and receiving and processing the answer signal in the separate control unit to recover the identification parameter and thereby identify the component, the step of processing further comprising the step of maintaining component records for the medical endoscopy system.

2. The method of claim 1, wherein said step of activating an identification procedure comprises initiating an operation step on the separate control unit.

3. The method of claim 1, wherein the data carrier comprises a memory for storing the data, and further comprising the step of updating the memory by transmitting a write signal from the separate control unit to the component via said inductive coupling.

4. The method of claim 1, further comprising the step of monitoring said identification procedure on a monitor by an operator.

5. The method of claim 1, further comprising the step of connecting the separate control unit to an overriding unit comprising a computer.

6. The method of claim 1, wherein each of said steps of transmitting the interrogation signal and of transmitting the answer signal further comprises using a high frequency data transmission system with the inductive coupling.

7. The method of claim 6, wherein each of said steps of transmitting the interrogation signal and of transmitting the answer signal further comprises modulating said interrogation signal and the answer signal before said transmitting via a pulse period modulation.

8. The method of claim 7, wherein each of said steps of receiving the interrogation signal and receiving the answer signal further comprises demodulating said interrogation signal and said answer signal after said transmitting.

9. A method for transmitting operational data between a first component of a medical endoscopy system and a separate control unit without physically connecting the component and the separate control unit, comprising the steps of:

effecting an inductive coupling between a data carrier of the first component and the separate control unit by positioning the data carrier of the first component in operational proximity to the separate control unit;

transmitting data representing an operational parameter of the first component from the data carrier to the separate unit via the inductive coupling;

receiving and processing the transmitted data at the separate unit to recover the operational parameter, said step of processing comprising the step of maintaining component records for the medical endoscopy system;

transmitting a control signal from the separate unit to the data carrier in response to said receipt and processing of the data; and regulating an operation of the first component using the transmitted control signal.

10. The method of claim 9, wherein said step of transmitting the data uses a high frequency data transmission system via the inductive coupling.

11. The method of claim 9, wherein said step of transmitting the data further comprises modulating the data before said transmitting and said step of receiving and processing the data further comprises demodulating said data after said transmitting using pulse period modulation.

12. The method of claim 9, further comprising the steps of:

effecting a second inductive coupling between a second component and the separate control unit by positioning a data carrier of the second component in operational proximity to one of the separate control unit and the data carrier of the first component;

transmitting second data representing an operational parameter of the second component from the data carrier of said second component to the separate control unit via the second inductive coupling;

receiving and processing the transmitted second data at the separate control unit;

transmitting a second control signal from the separate control unit to the data carrier of the second component and to the data carrier of the first component in response to the receipt and processing of the second data; and regulating an operation of the first component and of the second component using the transmitted second control signal.

13. The method of claim 9, further comprising the steps of:

activating an identification procedure by transmitting an identification interrogation signal from the separate control unit to the component via the inductive coupling;

receiving the identification interrogation signal at the component;

reading an identification parameter from the data carrier in response to said receipt of the identification interrogation signal;

transmitting, from the data carrier to the separate control unit via the inductive coupling, an answer signal indicating the identification parameter read from the data carrier; and receiving and processing the answer signal in the separate control unit to recover the identification parameter and thereby identify the component.

14. A device for automated identification of a component of a medical endoscopy system using data stored on the component, comprising:

a data carrier of the component, said data carrier including a memory for storing data comprising a parameter of the component;

a control unit, separate from and unconnected to said data carrier, comprising a read-write controller;

an energy and data transmission system in each of the component and the control unit for bidirectionally transmitting data signals between said data carrier and said control unit via an inductive coupling when said data carrier is brought within an operational proximity of said control unit;

a modulation and demodulation unit in said control unit and connected to said read-write controller for modulating and demodulating transmitted data signals; and an emitting-receiving device in the component and connected to said data carrier for emitting data signals to said component and for receiving data signals from said component and for directing power to the component from said control unit via the inductive coupling.

15. The device of claim 14, wherein said data transmission system comprises an inductive high frequency transmission system.

16. The device of claim 15, wherein said modulation and demodulation unit operatively modulates the data signals using pulsed period modulation.

17. The device of claim 14, wherein the data signals transmitted between said data carrier and said read-write controller have a specific frame structure, said frame structure comprising:

an identification code;

at least one data post following the identification code; and a check code following said at least one data post for use in recognizing an error in said at least one data post.

18. The device of claim 14, further comprising an operating device connected to said read-write controller and operable for activating a component identification procedure.

19. The device of claim 18, further comprising a monitor connected to said control unit for monitoring said component identification procedure.

20. The device of claim 19, further comprising an overriding device connected to said read-write controller, said operating device, and said monitor.

21. The device of claim 14, further comprising a write head in said read-write controller for transmitting data to said data carrier and writing data to said memory of said data carrier.

22. A device for automated adjustment of an operational parameter of a component of a medical endoscopy system, comprising:

a data carrier of the component including data representing an operational parameter of the component;

said data carrier being operationally connected to a portion of the component such that an adjustable parameter of said portion is adjustable in response to a signal transmitted from said data carrier to said portion;

a controller separate and unconnected to said data carrier;

an energy and data transmission system in each of the component and said controller for transmitting power from said controller to said data carrier, and for transmitting data representing said operational parameter from said data carrier to said controller, via an inductive coupling when said data carrier is within an operational proximity of said controller;

said controller being operable for transmitting a signal for adjusting said adjustable parameter through said energy and data transmission system in response to receipt by said controller of the data representing said operational parameter; and said data carrier being operable for receiving said transmitted signal and transmitting said received signal to said portion of the component.

23. The device of claim 22, wherein said energy and data transmission system comprises a high frequency transmission system using said inductive coupling.

24. The device of claim 22, wherein said energy and data transmission system includes a modulation-demodulation unit for producing a pulsed period modulation of the data transmitted between said data carrier and said controller.

25. The device of claim 22, further comprising:

a memory in said data carrier, for storing information representing at least one of a serial number, a maintenance history, and an operational duration of the component; and said controller being operable for interrogating said memory and for writing to said memory through said energy and data transmission system.

26. The device of claim 22, wherein the component comprises a camera head of an endoscope system.

* * * * *